(12) United States Patent
Lim (10) Patent No.: US 8,359,099 B2
(45) Date of Patent: Jan. 22, 2013

(54) TORQUE WRENCH ACTUATED OPEN PASSAGE SEPTUM

(75) Inventor: Wisit Lim, Palmdale, CA (US)

(73) Assignee: Pacesetter, Inc., Sylmar, CA (US)

( * ) Notice: Subject to any disclaimer, the term of this patent is extended or adjusted under 35 U.S.C. 154(b) by 345 days.

(21) Appl. No.: 12/777,897

(22) Filed: May 11, 2010

(65) Prior Publication Data

US 2011/0282410 A1 Nov. 17, 2011

(51) Int. Cl.
*A61N 1/375* (2006.01)
(52) U.S. Cl. .......................................... 607/37
(58) Field of Classification Search .............. 607/36–37
See application file for complete search history.

(56) References Cited

U.S. PATENT DOCUMENTS

| | | | |
|---|---|---|---|
| 5,252,090 A * | 10/1993 | Giurtino et al. | 439/441 |
| 5,509,928 A | 4/1996 | Acken | |
| 7,155,283 B2 | 12/2006 | Ries et al. | |
| 7,231,253 B2 | 6/2007 | Tidemand et al. | |
| 8,145,314 B2 * | 3/2012 | McDonald | 607/37 |
| 2004/0122481 A1 | 6/2004 | Tidemand et al. | |
| 2004/0232597 A1 | 11/2004 | Sjostedt et al. | |
| 2005/0131481 A1 | 6/2005 | Ries et al. | |
| 2005/0131483 A1 | 6/2005 | Zhao et al. | |

* cited by examiner

*Primary Examiner* — Carl H Layno
*Assistant Examiner* — Paula J Stice (57) ABSTRACT

A septum for use in an implantable pulse generator. The septum includes a soft sealing material and a hard inner portion or core having a set of lips. The lips are exposed outside the soft sealing material and act to displace the sealing material when a force is applied, for example from a tool used to tighten or loosen a set screw, enlarging a slit, seam or slot into a passageway through the septum.

19 Claims, 12 Drawing Sheets

TORQUE WRENCH ACTUATED OPEN PASSAGE SEPTUM

FIELD OF THE INVENTION

The present invention relates to implantable medical devices. More specifically, the present invention relates to a septum for an implantable medical device.

BACKGROUND OF THE INVENTION

Implantable medical devices, such as pacemakers, implantable cardioverter defibrillators (ICD), etc., are implanted in patients in order to supply electrical pulses to a patient's heart to maintain a consistent heartbeat. Some devices may additionally function as a defibrillator, detecting cardiac arrhythmia and providing an extra surge of electricity to prevent heart damage. These devices are inserted in a patient's chest and electrical leads extending from the device, are thread through a vein to the patient's heart. The device housing and the leads are hermetically sealed in order to prevent the electrical connections from shorting due to bodily fluids. The electrical leads have electrodes, defibrillator coils, and/or sensors placed at various positions on and within the heart. The electrodes and defibrillator coils provide electrical current to stimulate the heart and the sensors determine whether a pulse is needed and how much current should be applied.

The electrical leads are thread through the housing of the device to reach the circuitry held within. The leads are then secured into position within the housing by a set screw received within the housing. The set screw is sealed from bodily fluids using a septum, which is made of silicone rubber and has a resealable split. The split allows a screwdriver, wrench or other tool to extend through the septum to tighten the set screw, the septum resealing after the tool is withdrawn from the case. Because the septum is made of silicone, the tool is able to push the silicone rubber aside to reach and tighten the set screw. However, the soft silicone rubber may prevent the tool from making full contact with the screw, as the soft material may be pulled downwards with the tool, covering the contact between the tool and the set screw. Additionally, as the tool enters the septum, small pieces of the silicone rubber are pulled off as the tool is pushed down. This tearing results in pieces of silicone rubber pushed into the socket of the set screw, which may cause the set screw to be stripped. Additionally, the cored silicone rubber causes the septum to contain holes and no longer be completely sealed, allowing bodily fluids to enter the septum. This leakage can potentially cause the electrical connections to short and cause the device to malfunction. Therefore, there is a need in the art for a septum that seals the electrical connections and allows a tool to enter in order to tighten a set screw without damaging the septum.

BRIEF SUMMARY OF THE INVENTION

A septum for use with an implantable pulse generator is disclosed herein. In one embodiment, the septum includes a body constructed of a first material and an inner portion or core constructed of a second material. The inner portion is substantially enclosed by the body, but includes a set of lips that is exposed at a top portion of the body. The top portion also includes a top face supporting the lips. The top face has multiple apertures to increase the flexibility of the inner portion. The lips deflect when a force, for example from a tool used to tighten a fastener, is applied downwards. When the lips bend, they displace the body, enlarging a slit, seam or slot within the body, allowing a tool to pass through the septum without substantially contacting the body of the septum.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Disclosed herein is a septum for use in an implantable pulse generator, such as, for example, a pacemaker or ICD. The septum body is made of a soft flexible material that can open and re-close, providing a seal. Inside the septum's body is an inner portion or core having lips or bevel faces that are exposed outside the body. The inner portion is made of a harder material than the body, but remains flexible through apertures. The apertures create a cantilever beam affect, where the beams elastically bend downwards when force is applied to the lips. The lips provide a contact surface for a tool, such as a torque wrench, to enter the septum. When force is applied to the lips, the inner portion deflects or deforms, displacing the body of the septum. The septum includes a slot that is formed throughout the entire body. As the inner portion deforms, the body is pulled apart at the slot, widening the slot into a passageway through which the tool may pass. Once the passageway has been widened, via the tool proximal end acting against the lips, the tool enters the septum and can tighten or loosen a set screw (included as part of the pulse generator) without damaging the body of the septum.

Figure 1:
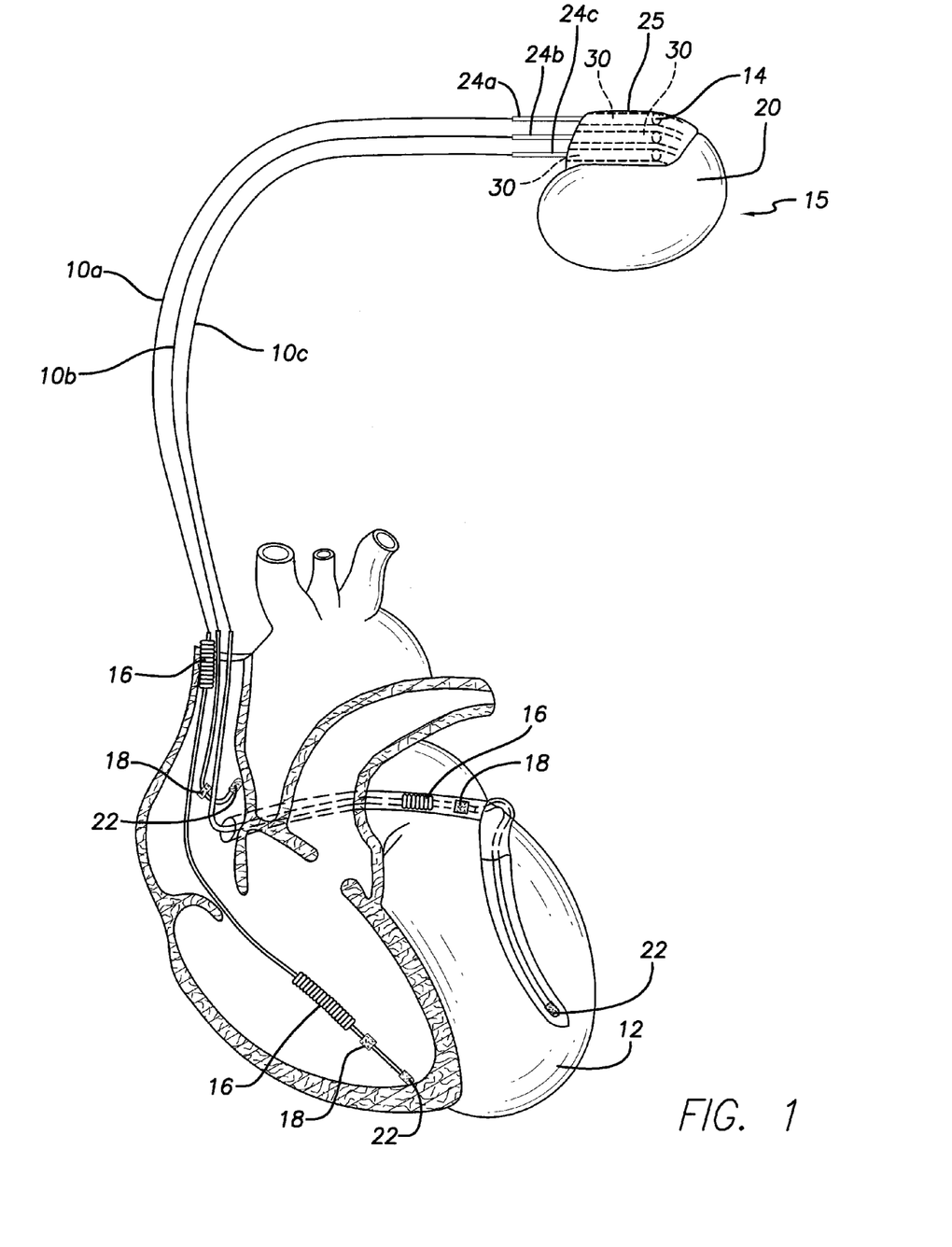
FIG. 1 is a partial cross sectional view of an anterior side of a heart, wherein a pulse generator is located nearby with three leads connected thereto and positioned on the heart.

For a general discussion of an embodiment of a pulse generator employing a septum, reference is made to FIG. 1, which is a partial cross-sectional view of an anterior side of a heart, wherein a pulse generator 15 is located nearby with three leads 10a, 10b, 10c connected thereto and the leads positioned on the heart 12. The pulse generator 15 may be a pacemaker, ICD, neurostimulator or any other implantable medical device housing electrical components. As indicated in FIG. 1, the pulse generator 15 may include a can 20, which houses the electrical components of the pulse generator 15, and a header 25. The header 25 may be mounted on the can 20 and may be configured to receive the lead connector ends 24a, 24b, and 24c in receptacles 30 of the header 25. Although three leads are illustrated, it should be appreciated that any number of leads may be implemented. For example, for cardiac resynchronization therapy (CRT) treatments, there may be two leads, one for each of the right and left ventricles and even, a third lead, for example, in the right atrium.

In one embodiment, as illustrated in FIG. 1, the leads 10a, 10b, 10c may include a tip electrode 22, a ring electrode 18 and a defibrillation coil 16. In some embodiments, the leads 10a, 10b, 10c may be configured to facilitate passive fixation and/or the lead may include features that facilitate passive fixation. In such embodiments, the tip electrode 22 may be in the form of a ring or domed cap and may form the distal tip of the lead 10a, 10b, 10c.

In some embodiments, the leads 10a, 10b, 10c may be configured for active fixation. In such embodiments, the tip electrodes may be in the form of a helical anchor that can be screwed through the tissue to fix the tip electrode 22 at the desired implant sight. The anchor electrode may be in the form of a helical anchor that is positioned in a fully extended state or may be extendable/retractable from a distal end of the lead body.

As shown in FIG. 1, in some embodiments, the leads 10a, 10b, 10c may include a defibrillation coil 16 about the outer circumference of the lead body 10a, 10b, 10c. The defibrillation coil 16 may be located proximal of the ring electrode 18. The ring electrodes 18 may extend about the outer circumference of the lead body 10a, 10b, 10c proximal of the tip electrode 22 of each lead 10a, 10b, 10c. In other embodiments, the leads 10a, 10b, 10c may include a greater or lesser number of electrodes 18 and 22, in different or similar configurations. In yet other embodiments, other lead components (e.g., additional ring electrodes, various types of sensors, etc. not shown) mounted on the lead body may be in electrical communication with the pulse generating device 15.

Figure 2:
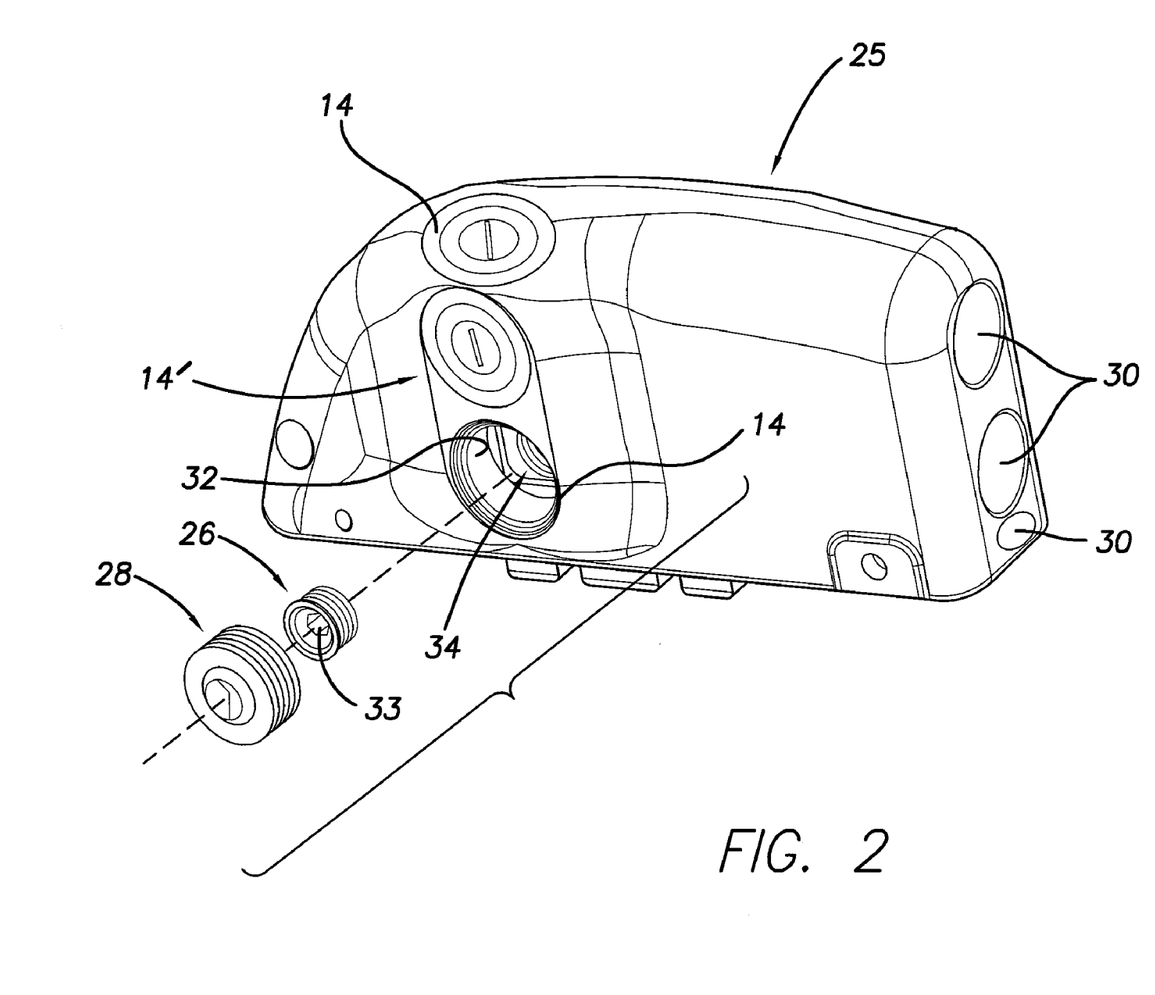
FIG. 2 is an isometric view of a header portion of the pulse generator.

FIG. 2 is an isometric view of the header 25 portion of the pulse generator 15. The header 25 receives the lead connector ends 24a, 24b, 24c via the respective receiving receptacles 30. Each connector assembly 14 of receptacle 30 may include a connector block 34, a set screw 26, and a septum 28. The connector blocks 34 electrically connect the electrical circuitry (not shown) within the pulse generator 15 to the lead connector ends 24a, 24b, 24c. The lead connector ends 24a, 24b, 24c may include contact rings and pins that may electrically contact the connector blocks 34 when the lead connector ends 24a, 24b, 24c are inserted into the receptacles 30. The contact rings and pins (not shown) are secured to the respective connector blocks 34, and as a result, the circuitry (not shown) via the set screw 26.

Each set screw 26 or fastener tightens the connection between a lead end 24a, 24b, 24c and the respective connector block 34 by pining the lead connector end 24a, 24b, 24c against the connector block 34. The set screw 26 is received within an aperture sidewall 32 and sealed from contact with bodily fluids by the septum 28. The set screw 26 may be threaded and be able to be tightened with a tool shaped to engage the set screw 26. For example, in some embodiments the set screw 26 may have an engagement feature 33 having a hexagonal shape for receiving and engaging a hex wrench tool. In other embodiments, the set screw 26 may have a linear engagement feature 33 for receiving and engaging a flat head tool. The septum 28 covers and seals the set screw 26 to prevent bodily fluids from making contact with the set screw 26.

Figure 3:
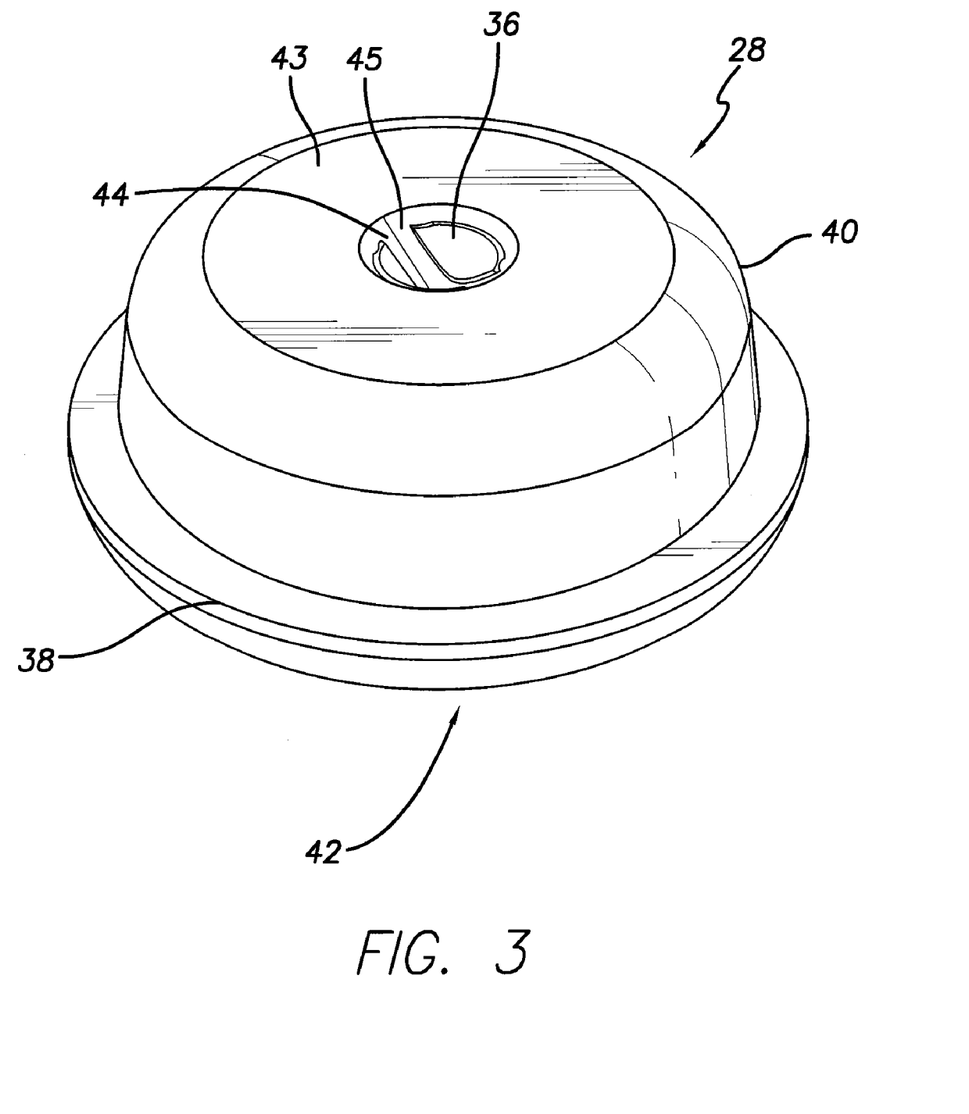
FIG. 3 is an isometric view of a septum.
Figure 4:
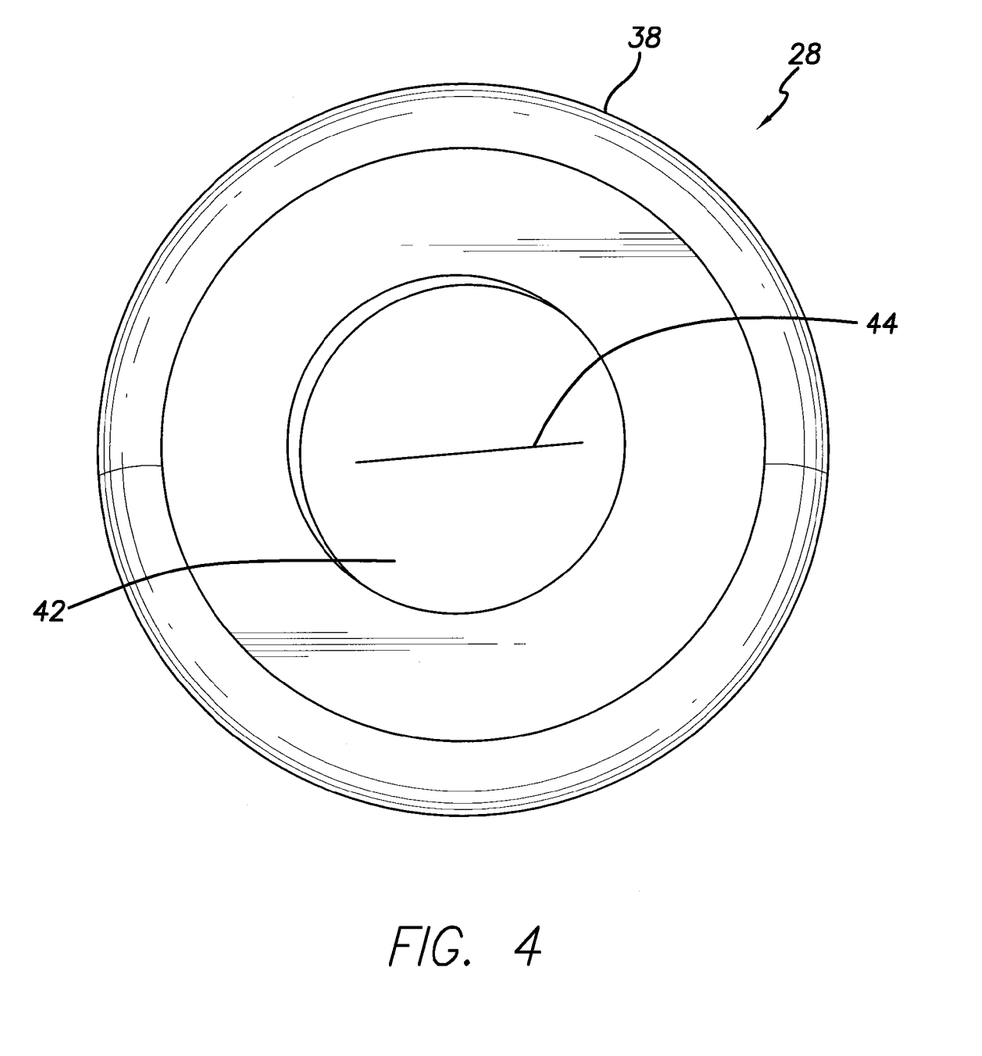
FIG. 4 is a bottom plan view of the septum.
Figure 5:
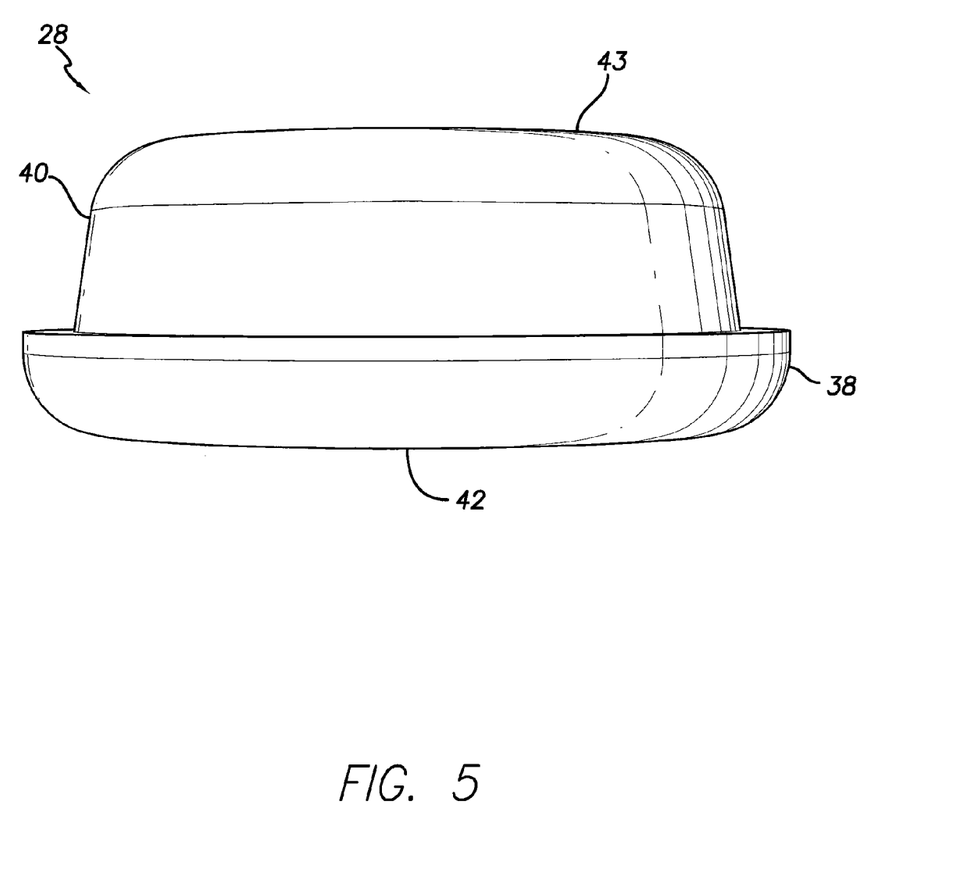
FIG. 5 is a side view of the septum.

The septum 28 allows a tool to enter and engage the set screw 26 for tightening or loosening, while also resealing when the tool is removed from the septum 28, preventing bodily fluids from entering the header 25 and contacting the set screw 26, connector block 34, or other electrical components of the device 15 or leads 24a, 24b, 24c. FIG. 3 illustrates an isometric view of the septum 28 according to some embodiments. FIGS. 4 and 5 illustrate a bottom plan view and a side view of the septum, respectively. Referring now to FIGS. 2, 3 and 5, the septum 28 covers the set screw 26. The septum 28 and set screw 26 may be dimensionally related, for example, the larger the diameter of the set screw 26 the larger the diameter of the septum 28. In some embodiments, the septum 28 may have a diameter of approximately 0.13 inch to approximately 0.18 inch.

The septum 28 has a body 40 that may be cylindrically shaped and includes an outer ring 38 that may have a larger diameter than the body 40. The outer ring 38 and the body 40 fit into the connector assembly 14 and seal the sidewall aperture 32 against bodily fluids. The body 40 and the ring 38 are constructed out of a flexible or resilient sealing material. In some embodiments, the body 40 and ring 38 are made of silicone rubber.

The septum 28 also includes a set of beveled faces or lips 36 that border a slit, seam or slot 44 in the body 40. The lips 36 are located on a top surface 43 of the body 40 and form an exterior of the inner portion 41 (shown in FIGS. 6-11). As can be understood from FIGS. 3 and 11, the lips 36 provide a surface for receiving a tool 70 used to tighten or loosen the set screw 26 threadably received in the connector block 34. The lips 36 are configured and located such that the tool may have minimum contact with the body 40 of the septum 28, while guiding the tool tip into and through the slot 44.

As can be understood from FIGS. 3 and 4, the top surface 43 and bottom portion 42 of the septum 28 each respectively includes the top and bottom ends of the slot 44. Thus, the slot 44 begins on the top portion 43 of the septum 28, between the lips 36, and extends throughout the entire body 40. The slot 44 allows the tool used to tighten or loosen a set screw 26 to pass through the septum 28 and reach the set screw 26. In some embodiments the bottom 42 of the septum 28 is placed on top of the set screw 26 within the connector assembly 14. In this embodiment, once the tool passes through the bottom end of the slot 44 on the bottom 42 of the septum 28, the tool may connect with the set screw 26. As shown in FIG. 3, the lips 36 may be located on either side of the slot 44 adjacent to the slot 44, the slot 44 and the lips 36 being located in a semi-spherical recess 45. The lips 36 may have an arcuate or curved surface that generally matches the curvature of the recess 45.

Figure 6:
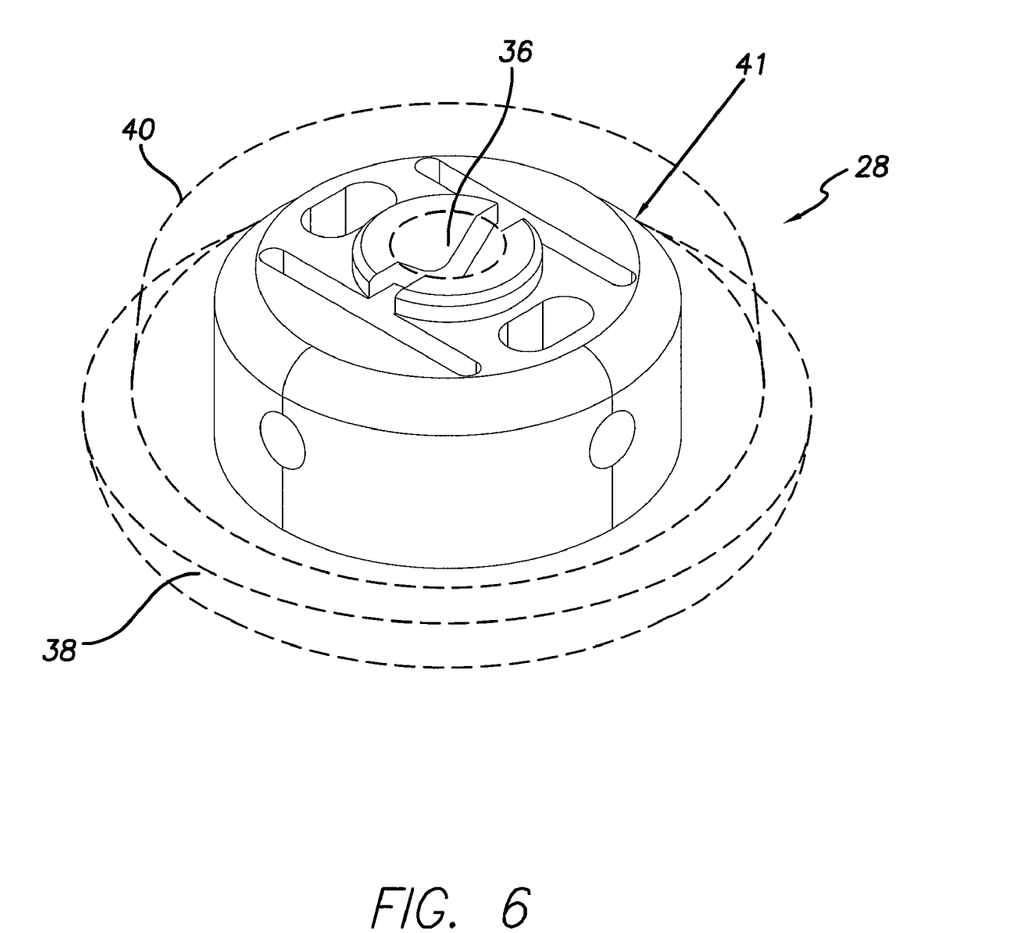
FIG. 6 is the same isometric view as FIG. 3, except the body of the septum is shown in phantom lines to illustrate the inner portion located in the body of the septum.

FIG. 6 is the same isometric view as FIG. 3, except that the body 40 of the septum 28 is shown in phantom lines to illustrate the inner portion or core 41 of the septum 28 located in the body 40. As illustrated in FIG. 6, the inner portion 41 of the septum 28 is substantially contained within the body 40 of the septum 28. In some embodiments, the inner portion 41 has a similar shape to the body 40 of the septum. For example, the body 40 may be cylindrically shaped, and the inner portion 41 may be cylindrically shaped as well. In some embodiments, the inner portion 41 has a smaller diameter than the body 40. It should be appreciated that the inner portion 41 may have any shape that fits within the body 40, and the inner portion 41 may be shaped differently than the body 40. The inner portion 41 includes the set of lips 36 that is exposed outside of the body 40. The inner portion 41 may be constructed of a relatively flexible hard material, and the inner portion 41 is harder than the material of the body 40. In some embodiments, the inner portion 41 is constructed out of hard plastic such as, for example, Polyoxymethylene (POM or DELRIN®), Polyetheretherketone (PEEK), Polysulfone (PSU), or etc. However, the inner portion 41 may be any other type of relatively flexible material that is also hard. For example, metal, alloys, metal doped plastic, etc. As the tool makes contact with the harder inner portion 41 of the septum 28, versus the body 40, the chance that the tool may damage the soft material of the body 40 is relatively small. Additionally, the inner portion 41 functions to substantially prevent the tool from contacting the body 40.

Figure 7:
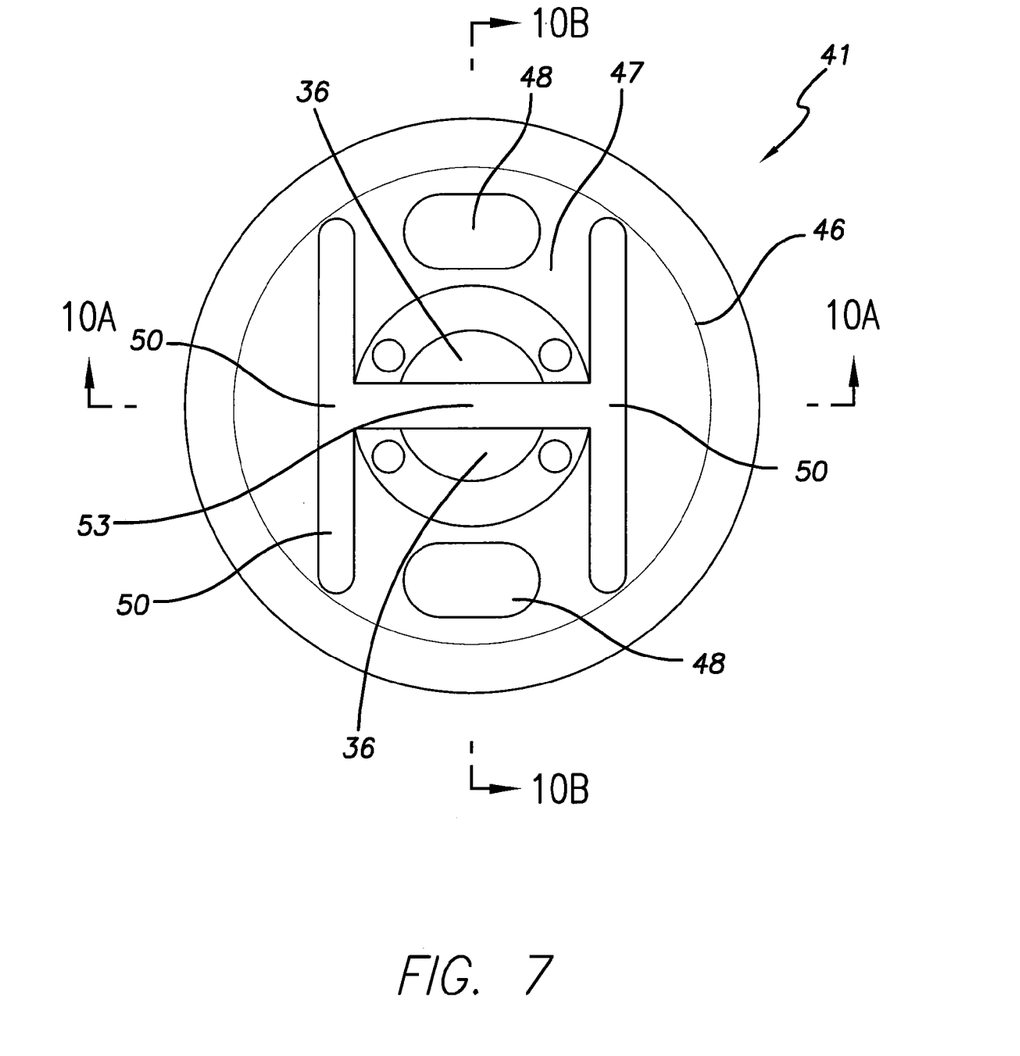
FIG. 7 is a top plan view of the inside portion of the septum removed from the body.

FIG. 7 illustrates a top plan view of the inner portion 41 removed from the body 40 of the septum 28. The inner portion 41 may be substantially hollow, allowing the body's 40 soft material to comprise a significant portion of the volume of septum 28. Additionally, the soft material of the body 40 infills the voids in the inner portion 41, such that the inner portion 41 is impregnated by the material of the body 40, thereby interlocking the inner portion 41 and body 40 to form the septum 28. The top face 46 of the inner portion 41 includes the lips 36, two lip rings 54 surrounding the lips 36, apertures 48, 50, 52 and a slot aperture 53.

The lip rings 54 surround and support the lips 36. As can be understood from FIG. 6, the lip rings 54 are covered by the body 40 of the septum 28. In some embodiments, the only part of the inner portion 41 not contained within the body 40 is the lips 36.

The apertures 48, 50 and 52 increase the flexibility of the inner portion 41. In some embodiments the apertures 48, 50 and 52 are filled with the soft material of the body 40 as the body 40 surrounds the inner portion 41. This arrangement helps to prevent bodily fluids from leaking into the set screw 26 assembly, as there are no unfilled apertures within the septum 28. Additionally, the mostly hollow inner portion 41 combined with the soft material of the body 40 allows the inner portion 41 to be constructed out of a harder material and still be flexible and allows the septum 28 to provide a seal for the set screw 26. The apertures 48, 50 and 52 include short apertures 48, cantilever apertures 50 and the lip ring apertures 52.

The short apertures 48 increase the flexibility of the inner portion 41 by reducing the support provided for the top face 46 and the lips 36. Similarly, the cantilever apertures 50 also act to increase the flexibility of the inner portion 41. The short apertures 48 and cantilever apertures 50 work together to allow the lips 36 to act as cantilever beams, and elastically deform or deflect downwards when force is applied to the lips 36. Specifically, the short apertures 48 define cantilever members 47 that extend between the portions of the top face 46 that include the lips 36 and rings 54 and the rest of the inner portion 41. The cantilever members 47, on account of their reduced cross sections, allow the lips 36 to deflect such that the short aperture 48 can widen as a tool distal end acts as a force and passes between the lips 36.

Figure 8:
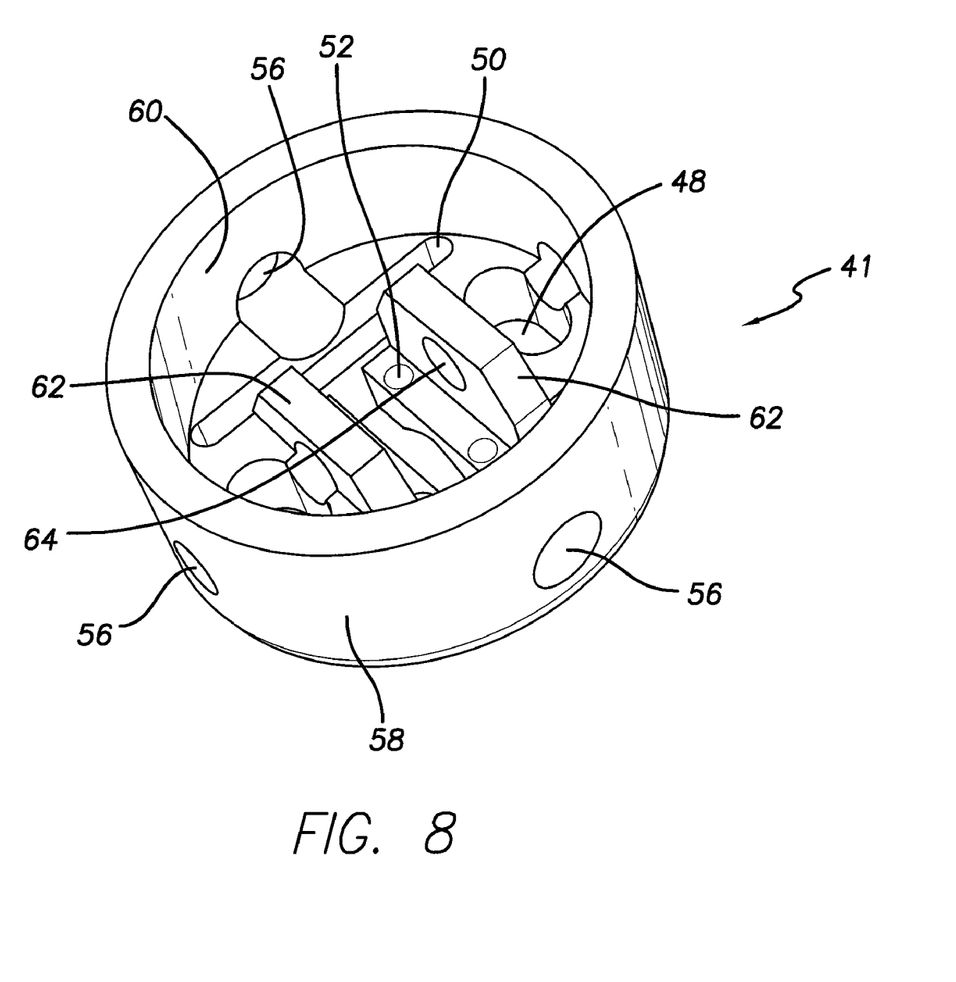
FIG. 8 is a bottom isometric view of the inner portion.
Figure 9:
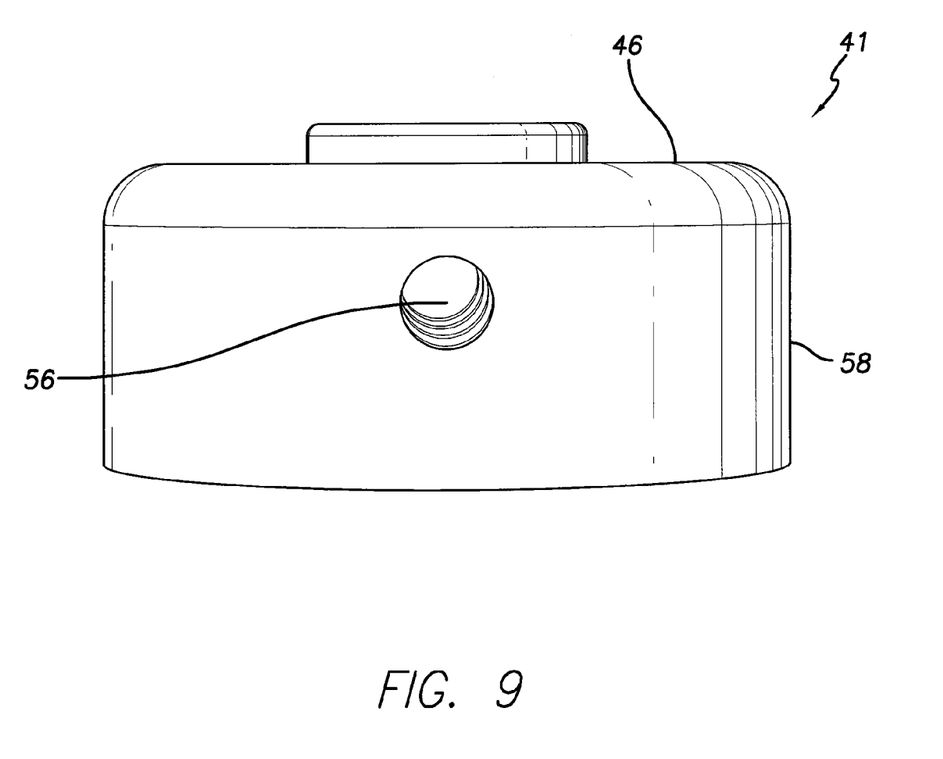
FIG. 9 is a side view of the inner portion.

FIG. 8 is a bottom isometric view of the inner portion 41. The inner portion 41 contains a sidewall 58 or outer circumferential surface that supports the top face 46 of the inner portion 41. The sidewall 58 may also be essentially perpendicular to the top face 46. The inner portion 41 has sidewall apertures 56 located along the sidewall 58. In some embodiments, the sidewall apertures 56 may be generally circular shaped. However, the sidewall apertures 56 may be any desired shape to allow the material of the body 40 to extend through the sidewall 58. Additionally, as can be understood from FIGS. 8 and 9, the sidewall apertures 56, in some embodiments, may be lined up such that each sidewall aperture 56 is spaced across from another sidewall aperture 56. In some embodiments there may be four sidewall apertures 56, such that two sidewall apertures 56 line up together and the other two sidewall apertures 56 line up together. The sidewall apertures 56, generally provide voids in the sidewall 58 of the inner portion 41 that allow the material of the body 40 to infill the inner portion 41 and cause the body 40 and inner portion 41 to be joined in an integrated or unitary septum 28.

Referring now to FIGS. 7 and 8, the inner portion 41 also includes lip walls 62 extending perpendicular from the lips 36. The lip walls 62 may have apertures 64 to allow the body 40 material to fill the apertures 64 and better secure the material of the body 40 to the inner portion 41 of the septum 28. The lip walls 62 may be formed integrally with the top face 46 of the inner portion 41, and in some embodiments the lip walls 62 may be essentially perpendicular to the top face 46. The lip walls 62 also may not extend as long as the sidewall wall 58 and may be suspended within the inner portion 41. The lip walls 62 may serve as a structural enhancement for the region of the body 40 that defines the slot 44. The lip walls 62 help to maintain the region of the body 40 that defines the slot 44 in a sealed state. For example, the lip walls 62 force the body material (e.g., silicone rubber) defining the slot 44 towards the center of the body 40 when the lips 36 are not being deflected. This action of lip walls 62 on the adjacent body material pushes the material of the body 40 closer together at the slot 44 area, thereby sealing the slot 44. When the lips 36 are caused to deflect, the lips walls 62 are caused to move downward and outward, pulling apart the region of the body 40 that defines the slot 44. Thus, as a tool pushes against the lips 36, the lip walls 62 bend downwards, pushing the body 40 of the septum 28 apart and widening the slot 44.

Figure 10A:
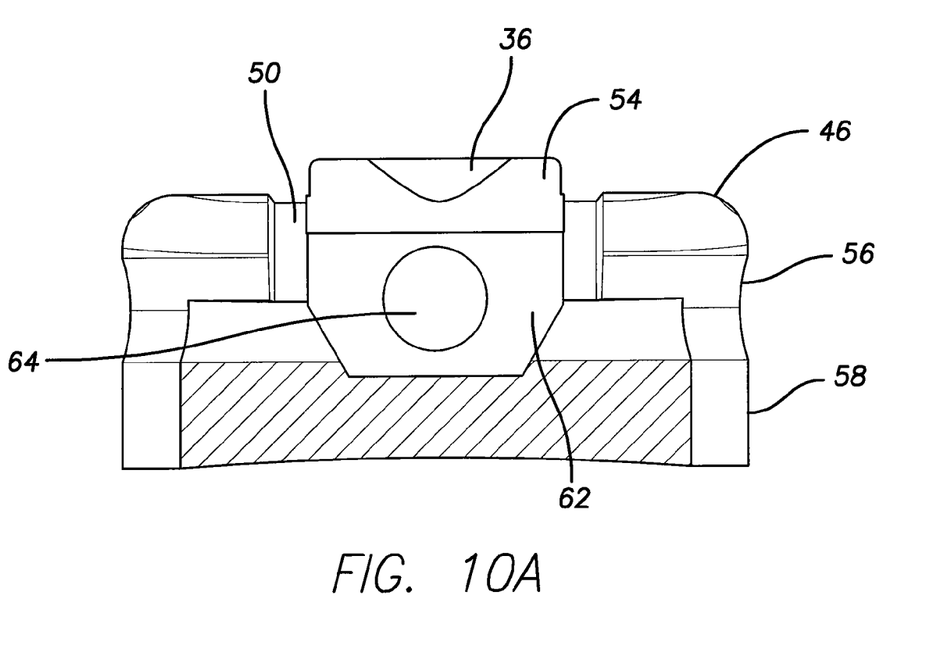
FIGS. 10A and 10B are cross-sectional views of the inner portion viewed along lines 10A-10A and 10B-10B as illustrated in FIG. 7, respectively.
Figure 10B:
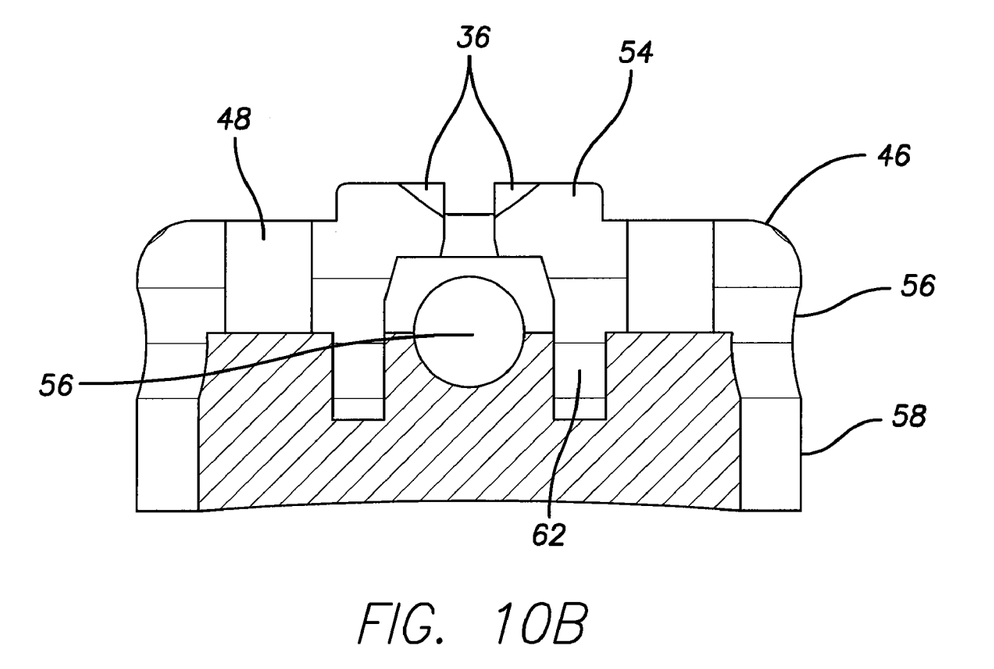

FIGS. 10A and 10B are cross sectional views of the inner portion 41 viewed along section lines 10A-10A and 10B-10B as shown in FIG. 7, respectively. As illustrated in FIG. 10A, in some embodiments, the apertures 64 of the lip walls 62 may be aligned, creating a passageway between the apertures 64 when the body 40 is not pressed and the lips 36 are not deflected. Additionally, the beam apertures 64 may be aligned with a set of the sidewall apertures 56, such that there is a passageway from one side of the sidewall 58 to the other side of the sidewall 58. Similarly, as illustrated in FIG. 11, the other set of side wall apertures 56 may be aligned to create another passageway through the inner portion 41.

Figure 11:
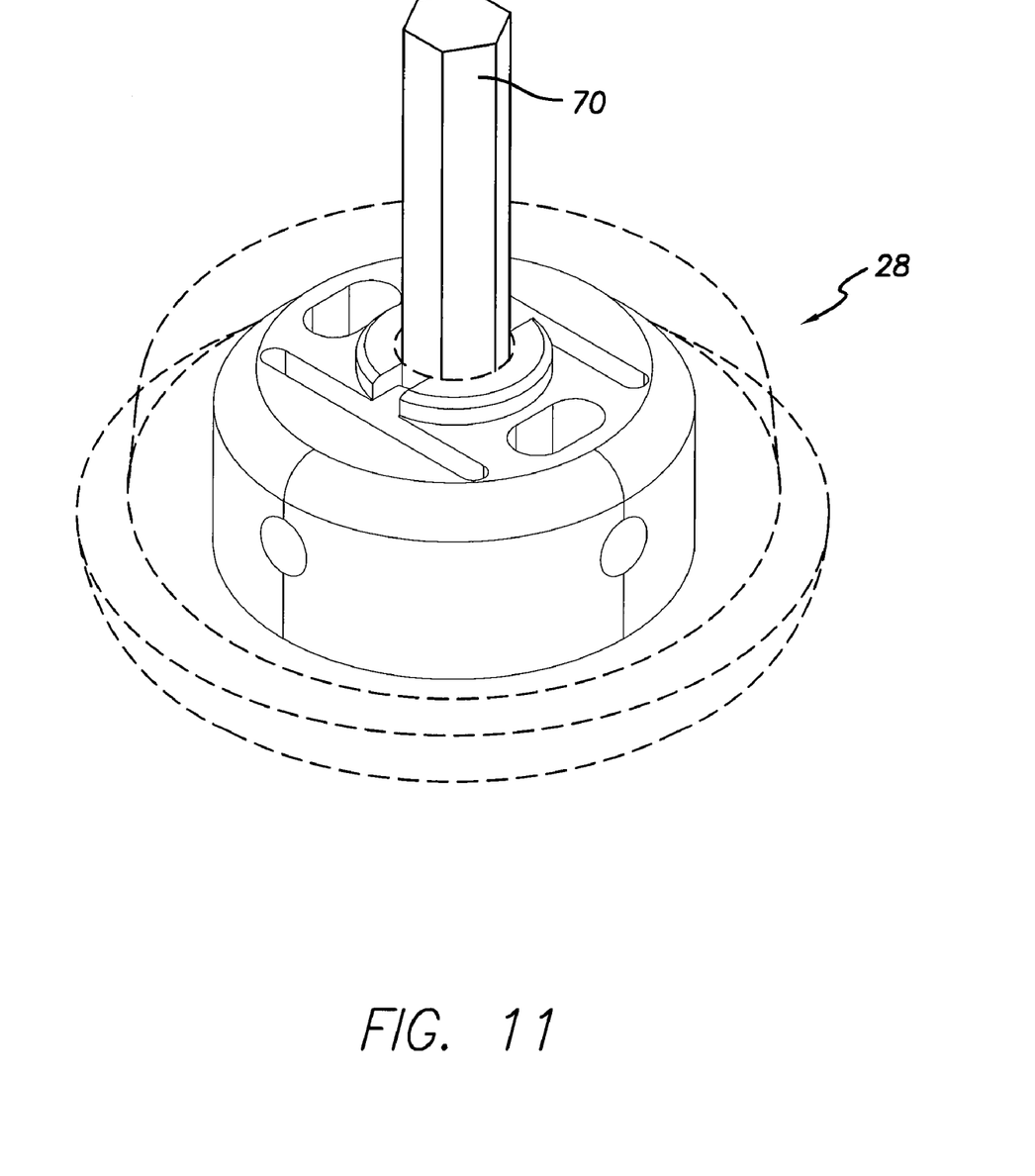
FIG. 11 is an isometric view of a tool being used along with the septum. wherein the body of the septum is shown in phantom lines to illustrate the inner portion of the septum located in the body.

FIG. 11 is an isometric view similar to FIG. 6, except illustrating the septum 28 receiving a tool 70 to tighten the set screw 26. Referring now to FIGS. 2 and 11, as the tool 70 applies a force against the lips 36, the lip walls 62 bend inwards towards the outer sidewall 58. As the lip walls 62 bend, the material of the body 40 located within the sidewall 58 of the inner portion 41 is displaced, enlarging the slot 44. The slot 44 is enlarged, allowing the tool 70 to enter the septum 28, without the engagement end of the tool substantially contacting the body 40. As the tool 70 travels through the inner portion 41 (via the slot 44), the engagement end of the tool 70 reaches the bottom 42 of the septum and exits through the bottom of the slot 44. The harder inner portion 41 is engaged by the tool 70 at the lips 36, the lip walls 62 being forced apart and causing the material of the body 40 defining the slot 44 to be spread apart to open a passage for the tool through the septum 28. As a result, the material of the body 40 defining the slot 44 is moved out of the way of the engagement end of the tool and contacts the shaft of the tool 70 with less force, if at all, preventing the septum 28 body 40 from being cored out while the tool 70 is inserted.

Once the engagement end of the tool 70 exits the slot 44, the engagement end of the tool 70 may then be able to engage the set screw 26, which is located adjacent the bottom 42 of the septum 28. As the engagement end of the tool 70 did not contact the body 40 when entering the septum 28, the material of the body 40 is not pulled into the engagement feature of the set screw 26, and therefore does not interfere with the engagement between the tool distal end and the set screw 26.

After the set screw 26 has been appropriately tightened and the tool 70 removed from the septum 28, the inner portion 41 returns to its original shape and the lip walls 62 are no longer deformed downwards. Once the lip walls 62 are in their original positions, the material of the body 40 seals the slot 44, the lip walls 62 adding structural support to maintain the slot 44 closed.

The septum 28 may be created in a variety of different manners. In some embodiments, the septum 28 may be made through injection molding the inner portion 41 or core, then injection molding or pouring the material of the body 40 around the inner portion 41. As the inner portion 41 has multiple apertures, the material of the body 40 may infill and surround the inner portion 41. Then, the slot 44 may be cut, via a mechanical device or a laser, through the material of the body 40. The slot 44 may be cut between the lips 36 and in line with the slot gap 53 in the inner portion 41.

The foregoing describes some example embodiments to achieve a self-sealing septum with an inner portion used to displace the body material and, thus, reduce the chance a tool will tear or damage the septum. Although the present invention has been described with reference to illustrated embodiments, persons skilled in the art will recognize that changes may be made in form and detail without departing from the spirit and scope of the invention. Indeed, in other embodiments, the septum may be used in other applications (besides implantable medical devices) to provide access to a fastener or tightening device while preventing other materials, such as liquids, from contacting the fastener. Accordingly, the specific embodiments described herein should be understood as examples and not limiting the scope of the disclosure.

What is claimed is:

1. A septum for use in an implantable pulse generator, comprising:
    a body constructed of a first material; and
    an inner portion constructed of a second material harder than the first material, wherein the body substantially surrounds the inner portion, the inner portion comprising a first lip, a second lip, and a top face, wherein the first lip and the second lip form a portion of an outer surface of the septum, and wherein the top face connects the first and second lips;
    an H-shaped aperture forming a cantilevered structure in the top face, wherein the H-shaped aperture comprises a slot aperture, a first cantilever aperture, and a second cantilevered aperture, wherein the first cantilever aperture is disposed at one end of the slot aperture and the second cantilever aperture disposed at an opposite end of the slot aperture, wherein the first and second cantilever apertures are oriented substantially perpendicular to a longitudinal axis of the slot aperture, and wherein the slot aperture forms a seam between the first lip and the second lip;
    wherein the first lip and the second lip deflect downwards when a downwards force is applied to the fist lip and the second lip.

2. The septum of claim 1, wherein the first material is silicone.

3. The septum of claim 1, wherein the second material is plastic.

4. The septum of claim 1, wherein the top face is contained within the body.

5. The septum of claim 1, wherein the body further comprises:
    a top portion boarding the first lip and the second lip;
    a bottom, wherein the bottom covers a bottom side of the inner portion; and
    a side extending between the top portion and the bottom;
    wherein the seam extends continuous from a location between the first lip and second lip to the bottom.

6. The septum of claim 5, wherein a width of the seam is enlarged when a downwards force is applied to the first lip and the second lip.

7. The septum of claim 6, wherein when the downwards force is applied to the first lip and the second lip, the first lip and the second lip deflect towards the bottom and displace the body and when no downwards force is applied to the first lip and the second lip, the inner portion acts on the body to decrease the width of the seam.

8. An implantable pulse generator for providing electrotherapy via an implantable lead, the implantable pulse generator comprising:
    a housing including an electronic component housed within the housing;
    a header connected to the housing, the header configured to receive the lead in an electrical connection with the electronic component within the housing;
    a fastener operatively connected to the header, wherein the fastener secures the electrical connection between the lead and the electronic component; and
    a septum, wherein the septum substantially covers the fastener, the septum comprising a body and a core substantially contained within the body, the core comprising a top face and a set of lips, the set of lips being exposed outside the body;
    an H-shaped aperture forming a cantilevered structure in the top face, wherein the H-shaped aperture comprises a slot aperture, a first cantilever aperture, and a second cantilevered aperture, wherein the first cantilever aperture is disposed at one end of the slot aperture and the second cantilever aperture disposed at an opposite end of the slot aperture, wherein the first and second cantilever apertures are oriented substantially perpendicular to a longitudinal axis of the slot aperture, and wherein the slot aperture forms a seam between the set of lips;
    wherein the set of lips deflect downwards when a downwards force is applied to the fist lip and the second lip.

9. The implantable pulse generator of claim 8, wherein the body is silicone rubber and the core is plastic.

10. The implantable pulse generator of claim 8, wherein:
    the body further comprises a top and a bottom operatively connected to each other; and
    the seam extends vertically from the top to the bottom.

11. The implantable pulse generator of claim 10, wherein the core enlarges a width of the slot when a downwards force is applied to the set of lips.

12. The implantable pulse generator of claim 11, wherein the set of lips deflects and displaces the body when the downwards force is applied.

13. The implantable pulse generator of claim 8, wherein the septum seals the fastener.

14. The implantable pulse generator of claim 8, wherein the fastener is a set screw.

15. The implantable pulse generator of claim 8, wherein the set of lips are supported on a cantilevered configuration of the core.

16. The implantable pulse generator of claim 15, wherein the core further comprises: a sidewall contained within the body; and a top face coupled to the sidewall, supporting the set of lips and substantially covered by the body, the cantilevered configuration being defined in the top face.

17. The implantable pulse generator of claim 16, the top face comprising a wall extending generally perpendicular to the top face and adjacent to at least one of the lips of the set of lips.

18. The implantable pulse generator of claim 8, wherein the body is softer than the core.

19. The implantable pulse generator of claim 8, wherein, when a force is applied to the set of lips, the core acts on the body to increase a width of a passageway of the seam, and wherein, when the force is removed from the set of lips, the core acts on the body to decrease the width of the passageway of the seam.

* * * * *